(12) United States Patent
Yen

(10) Patent No.: US 9,692,003 B2
(45) Date of Patent: Jun. 27, 2017

(54) PHENANTHROLINE DERIVATIVE AND USE THEREOF

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 308 days.

(21) Appl. No.: 14/686,794

(22) Filed: Apr. 15, 2015

(65) Prior Publication Data
US 2016/0308159 A1 Oct. 20, 2016

(51) Int. Cl.
*H01L 51/50* (2006.01)
*C07D 471/04* (2006.01)
*H01L 51/00* (2006.01)

(52) U.S. Cl.
CPC ........ *H01L 51/5072* (2013.01); *C07D 471/04* (2013.01); *H01L 51/0072* (2013.01); *H01L 51/0067* (2013.01); *H01L 51/5096* (2013.01)

(58) Field of Classification Search
CPC ............ H01L 51/5072; H01L 51/0072; H01L 51/5096; H01L 51/0067; C07D 471/04
USPC ....................................................... 428/690
See application file for complete search history.

(56) References Cited

U.S. PATENT DOCUMENTS 7,119,204 B2 * 10/2006 Lecloux ............... C07C 211/49
546/81
7,282,586 B1   10/2007 Yen et al.
7,754,348 B2 *  7/2010 Yen ..................... C07D 471/04
313/504
7,982,213 B2 *  7/2011 Okajima ............. C07D 471/04
257/40
8,114,529 B2    2/2012 Kitazawa et al.

* cited by examiner

*Primary Examiner* — Michael M Bernshteyn

(57) ABSTRACT

The present invention discloses a phenanthroline derivative is represented by the following formula(I), the organic EL device employing the phenanthroline derivative as hole blocking electron transport material, electron transport material can display good performance like as lower driving voltage and power consumption, increasing efficiency and half-life time.

formula(I)

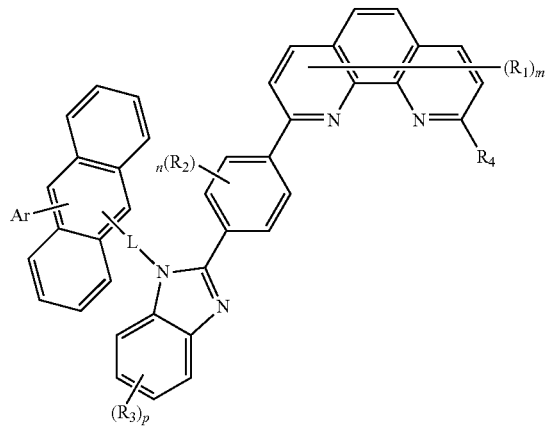

wherein Ar, m, n, p and $R_1$ to $R_4$ are the same definition as described in the present invention.

10 Claims, 1 Drawing Sheet

| 13 | — metal electrode |
| 12 | — electron injection layer |
| 11 | — electron transport layer |
| 10 | — hole blocking layer |
| 9 | — emitting layer |
| 8 | — hole transport layer |
| 7 | — hole injection layer |
| 6 | — transparent electrode |

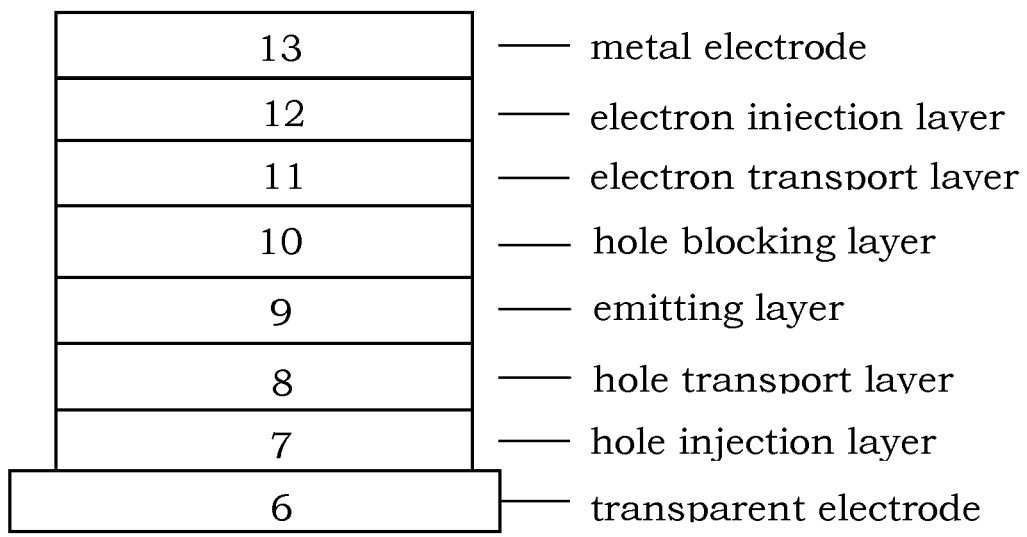

PHENANTHROLINE DERIVATIVE AND USE THEREOF

FIELD OF INVENTION

The present invention generally relates to a phenanthroline derivative and organic electroluminescent (herein referred to as organic EL) device using the derivative. More specifically, the present invention relates to the derivative having general formula(I), an organic EL device employing the derivative as hole blocking electron transport material (herein referred to as HBETM), electron transport material (herein referred to as ETM).

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL is composed of layers of organic materials situated between two electrodes, which include a hole transporting layer (HTL), an emitting layer (EML), an electron transporting layer (ETL). The basic mechanism of organic electroluminescence involves the injection of the carrier, transport, recombination of carriers and exciton formed to emit light. When an external voltage is applied to an organic light-emitting device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden. Thus, a fluorescence electroluminescent device has only 25% internal quantum efficiency. In contrast to fluorescence electroluminescent device, phosphorescent organic light-emitting diodes make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC).

The phosphorescent organic EL utilizes both triplet and singlet excitons. Cause of longer life time and the diffusion length of triplet excitons compared to those of singlet excitons, the phosphorescent organic EL generally need an additional hole blocking layer (HBL) between the emitting layer (EML) and the electron transporting layer (ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, the good thermal and electrochemical stability of the materials are also needed.

Currently, 2,9-dimethyl-4,7-diphenyl-1,10-phenanthroline (BCP), bathophenanthroline (Bphen) have been used as the typical materials for the HBL and HBETL of phosphorescent OLED. However, phenanthroline derivatives exhibit lower Tg (Bphen:55° C., BCP:65° C.), lower heat-resistant (Td: Weight loss <0.5% at 240° C. for Bphen and 260° C. for BCP). It's difficult to operate under deposition process and its devices show lower stability and short half-life time. U.S. Pat. No. 7,119,204 disclose a series of substituted-phen anthroline derivatives, as electron-transporting materials. U.S. Pat. No. 7,282,586 disclose a specific phenanthroline derivative 2,9-bis(5-(biphenyl-4-yl)-1,3,4-oxadiazol-2-yl)-1,10-phenanthroline, as an electron transporting material, compare with conventional 2,9-dimethyl-4,7-diphenyl-1,10-phenanthroline (BCP), the drive voltage is decreased from 8V to 7V at 2000 cd/m$^2$, and higher current efficiency is achieved. U.S. Pat. No. 7,754,348 disclose a series of 2,9-substituted phenanthroline derivatives as electron transporting material, higher operate life time and higher luminance than comparable example 1-3 and Alq3 has also been achieved at a driving voltage of 5V. U.S. Pat. No. 7,982,213 disclose a series of aryl substituted phenanthroline, a phosphorescent organic EL using the phenanthroline compound as HBETL provided high efficiency and a high luminance and has a high long-term durability. U.S. Pat. No. 8,114,529 disclose a series of bis-phenanthroline skeleton compounds, by using phenanthroline compounds as HBETL, a phosphorescent organic EL having low driving voltage and excellent durability.

There continues to be a need for organic EL materials which is able to efficiently transport electrons and block holes, with good thermal stability and high emitting efficiency. According to the reasons described above, the present invention has the objective of resolving such problems of the prior-art and offering a light emitting device which is excellent in its thermal stability, high luminance efficiency, high luminance and long half-life time. The present invention disclose a novel phenanthroline derivative having general formula(I), used as hole blocking electron transport material (HBETM) or electron transport material (ETM) have good charge carrier mobility and excellent operational durability can lower driving voltage and power consumption, increasing efficiency and half-life time of organic EL device.

SUMMARY OF THE INVENTION

Provided a phenanthroline derivative can use as hole blocking electron transport material (HBETM) or electron transport material (ETM) for organic EL device. The phenanthroline derivative can overcome the drawbacks of the prior materials like as lower efficiency, half-lifetime and higher power consumption.

An object of the present invention is to provide the phenanthroline derivative which can be used as hole blocking electron transport material (HBETM) or electron transport material (ETM) for organic EL device.

The present invention has the economic advantages for industrial practice. Accordingly the present invention, the phenanthroline derivative which can be used for organic EL device is disclosed. The mentioned the phenanthroline derivative represented by the following formula(I):

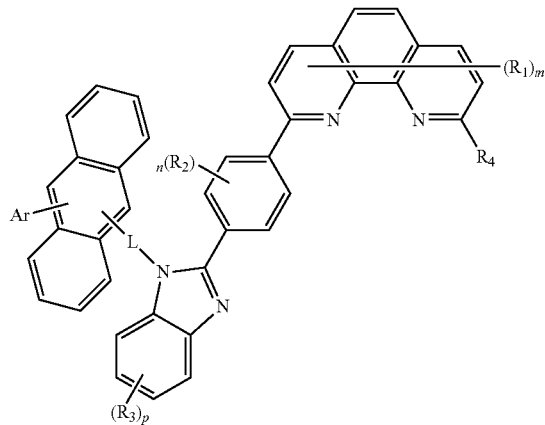

formula(I)

wherein L represents a substituted or unsubstituted arylene group having 6 to 30 ring carbon atoms, m represents an integer of 0 to 6, n represents an integer of 0 to 4, p represents an integer of 0 to 4; Ar is a substituted or unsubstituted aryl group having 6 to 50 ring carbon atoms, provided that Ar represents a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, and a substituted or unsubstituted chrysenyl group; $R_1$ to $R_4$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

BRIEF DESCRIPTION OF THE DRAWINGS

FIG. 1 show one example of organic EL device in the present invention, and 6 is transparent electrode, 13 is metal electrode, 7 is hole injection layer which is deposited onto 6, 8 is hole transport layer which is deposited onto 7, 9 is fluorescent or phosphorescent emitting layer which is deposited onto 8, 10 is hole blocking layer which is deposited onto 9, 11 is electron transport layer which is deposited onto 10, 12 is electron injection layer which is deposited on to 11.

DESCRIPTION OF THE PREFERRED EMBODIMENTS

What probed into the invention is the phenanthroline derivative and organic EL device using the phenanthroline derivative. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the phenanthroline derivative which can be used as hole blocking electron transport material (HBETM) or electron transport material (ETM) for organic EL device are disclosed. The mentioned phenanthroline derivative represented by the following formula(I):

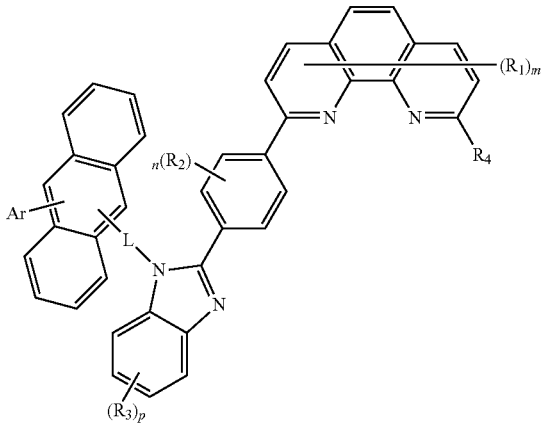

formula(I)

wherein L represents a substituted or unsubstituted arylene group having 6 to 30 ring carbon atoms, m represents an integer of 0 to 6, n represents an integer of 0 to 4, p represents an integer of 0 to 4; Ar is a substituted or unsubstituted aryl group having 6 to 50 ring carbon atoms, provided that Ar represents a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, and a substituted or unsubstituted chrysenyl group; $R_1$ to $R_4$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the phenanthroline derivative formula(I), wherein Ar represented the follows:

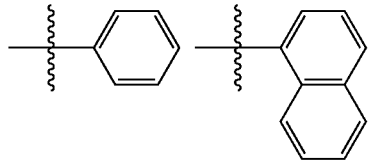

-continued

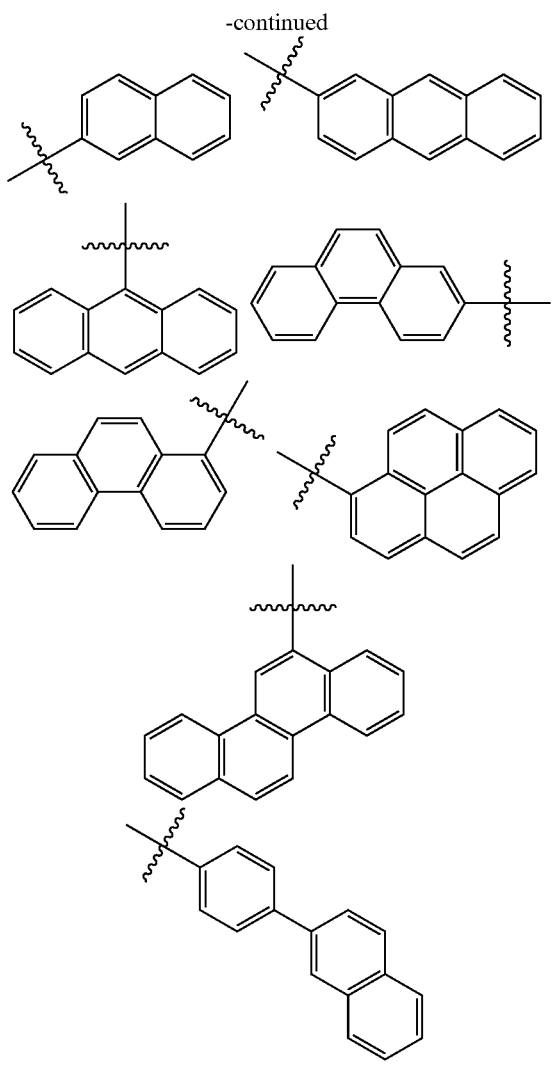

According to the above-mentioned the phenanthroline derivative formula(I) represented by the following formula (II):

formula(II)

wherein L represents a substituted or unsubstituted arylene group having 6 to 30 ring carbon atoms, m represents an integer of 0 to 6, n represents an integer of 0 to 4, p represents an integer of 0 to 4; Ar is a substituted or unsubstituted aryl group having 6 to 50 ring carbon atoms, provided that Ar represents a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, and a substituted or unsubstituted chrysenyl group; $R_1$ to $R_4$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the phenanthroline derivative formula(II), wherein Ar represented the follows:

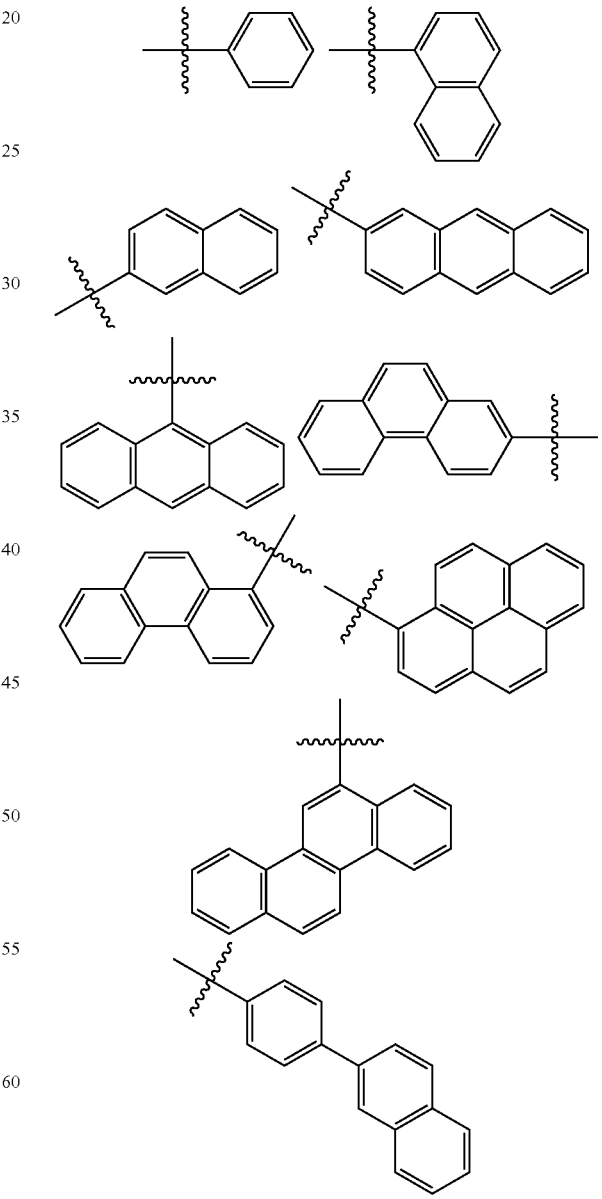

In this embodiment, some phenanthroline derivatives are shown below:

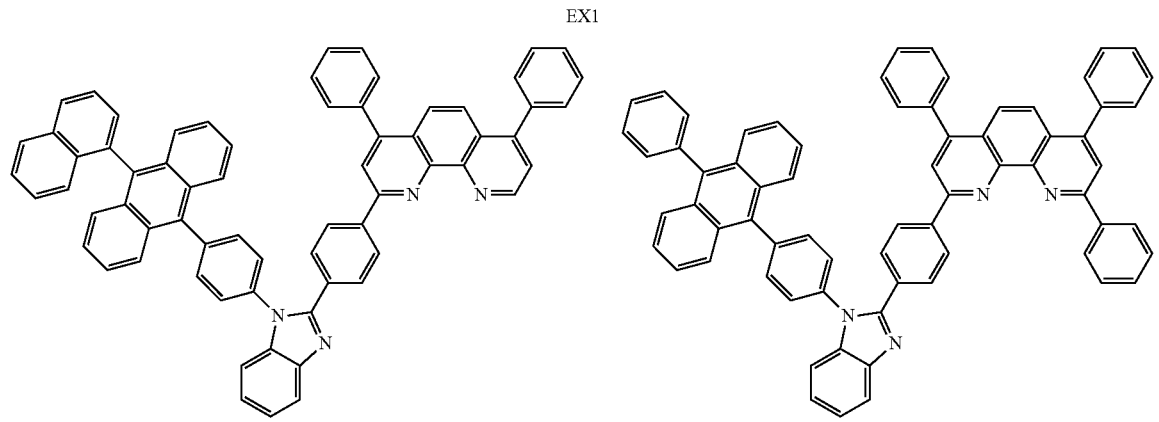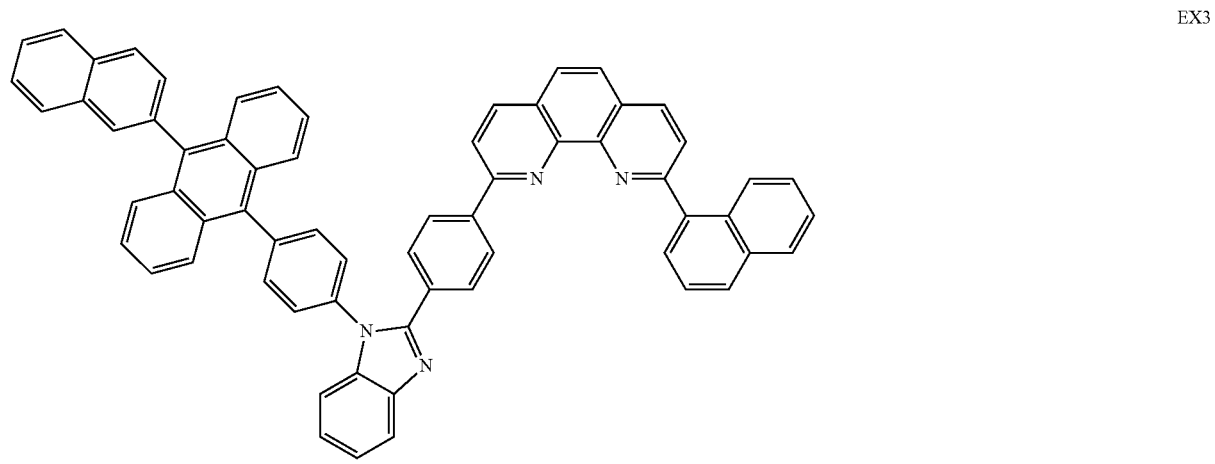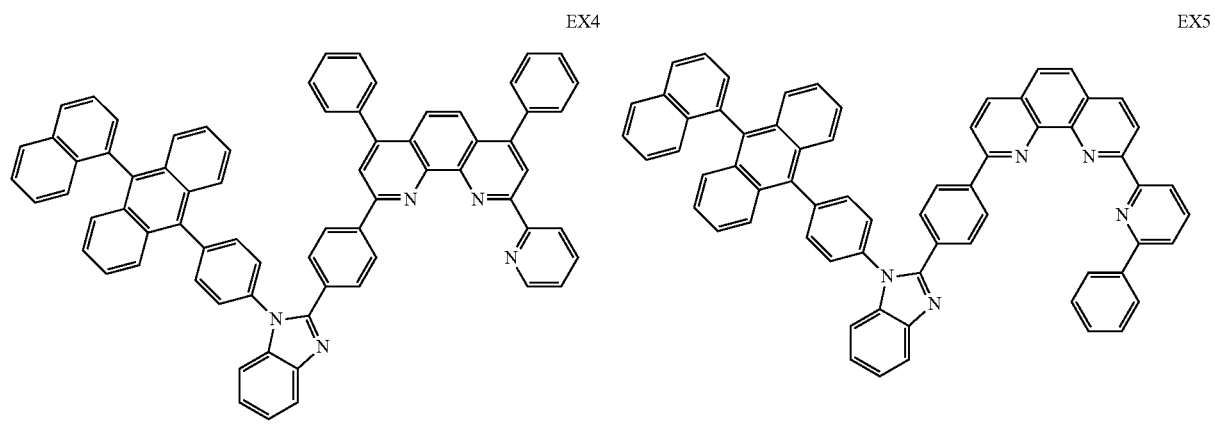

-continued
EX6
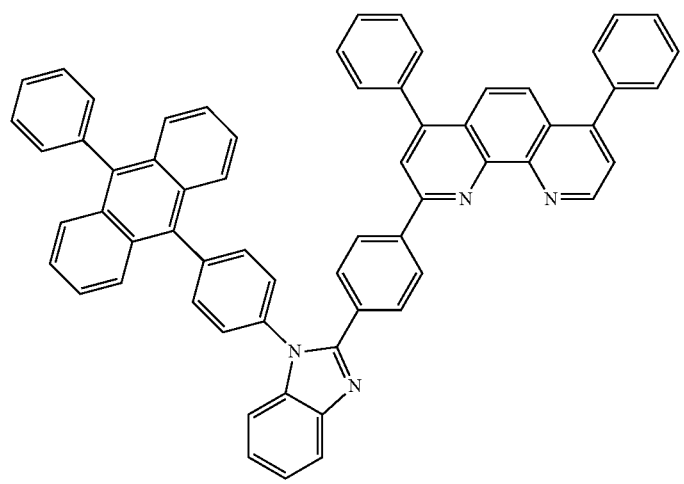
EX7
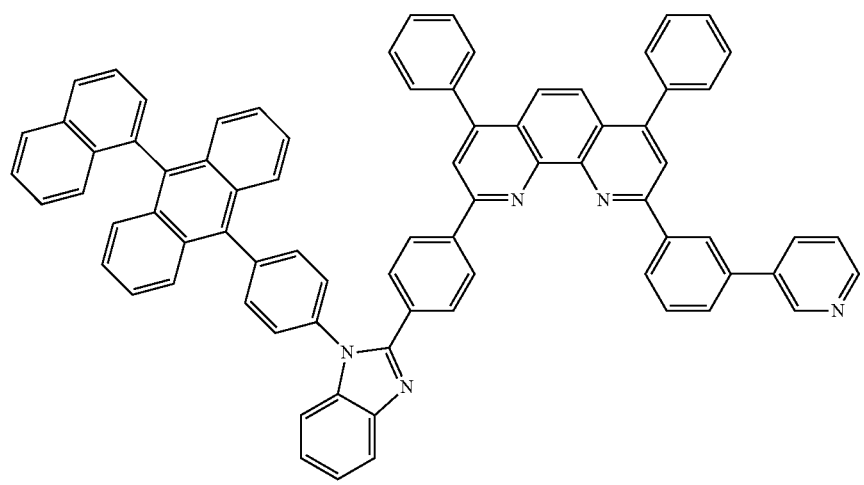
EX8
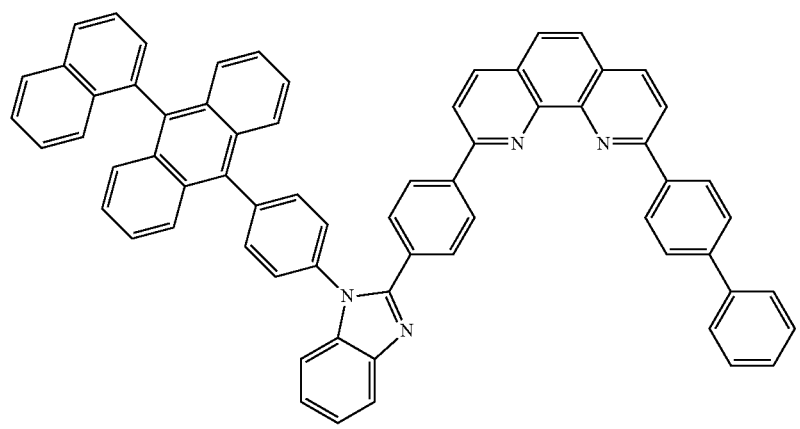

-continued
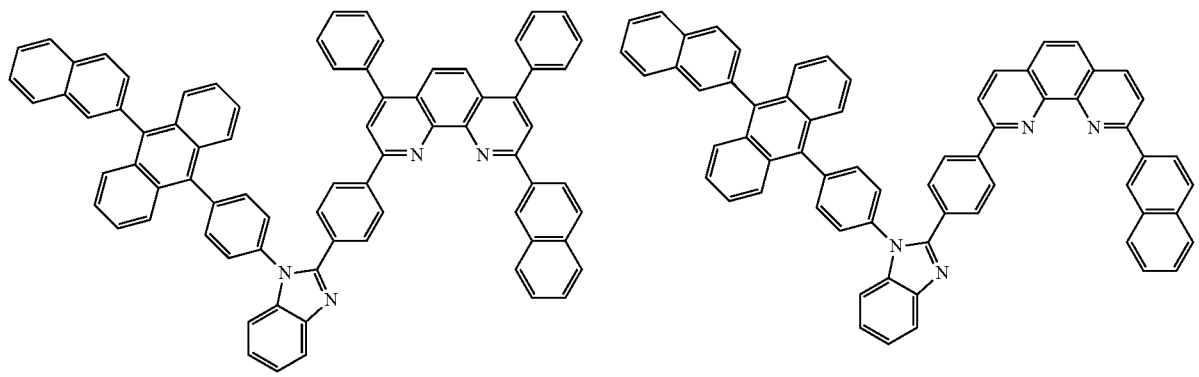
EX9
EX10
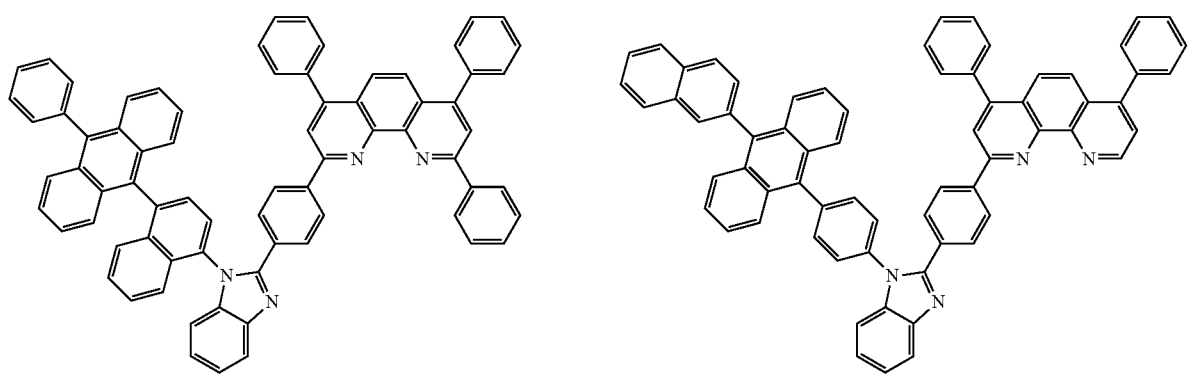
EX11
EX12
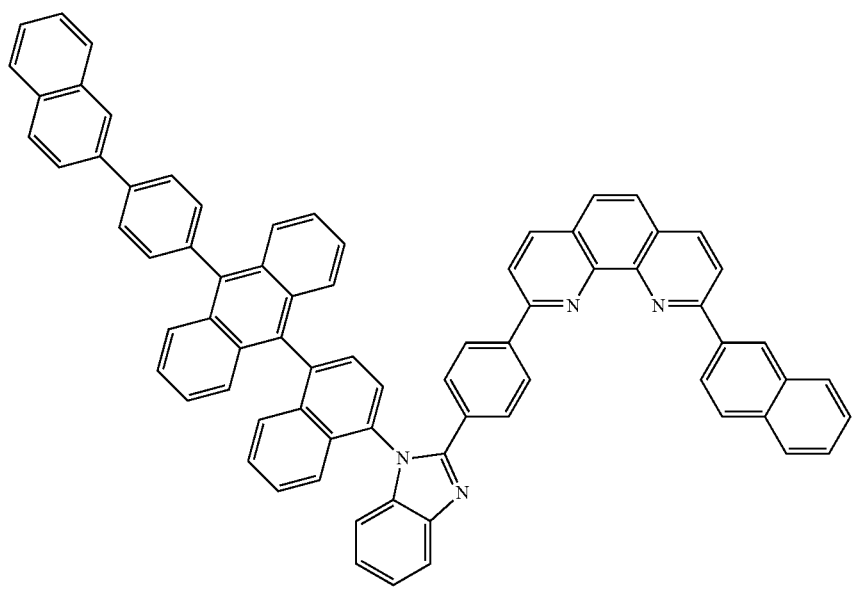
EX13

-continued
EX14
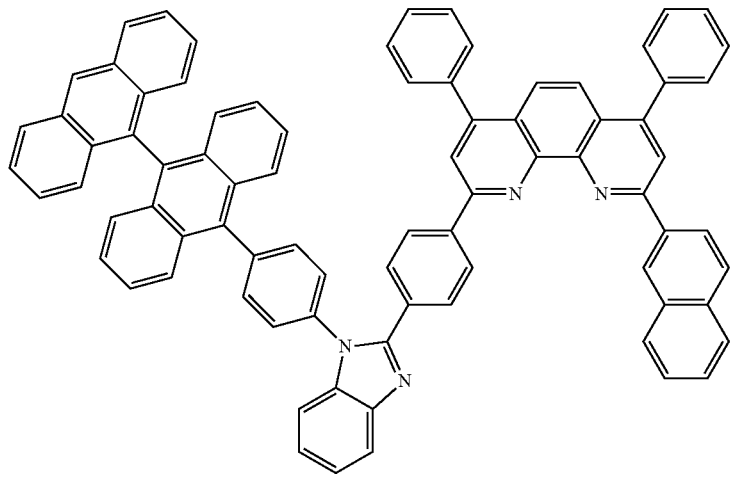
EX15
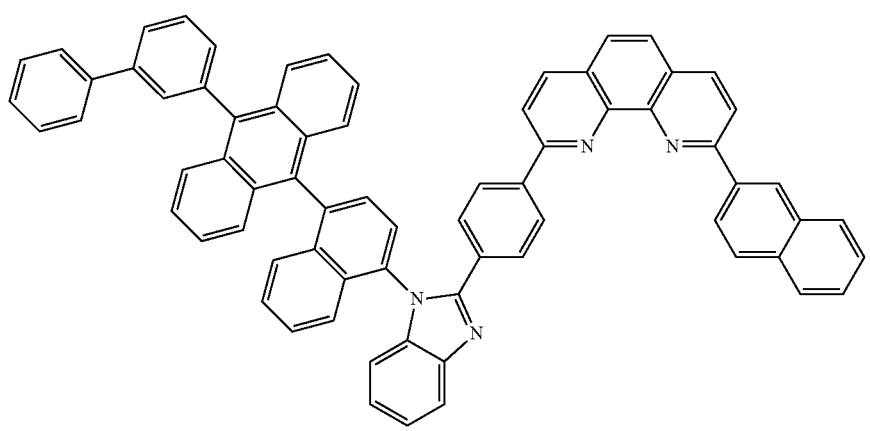
EX16
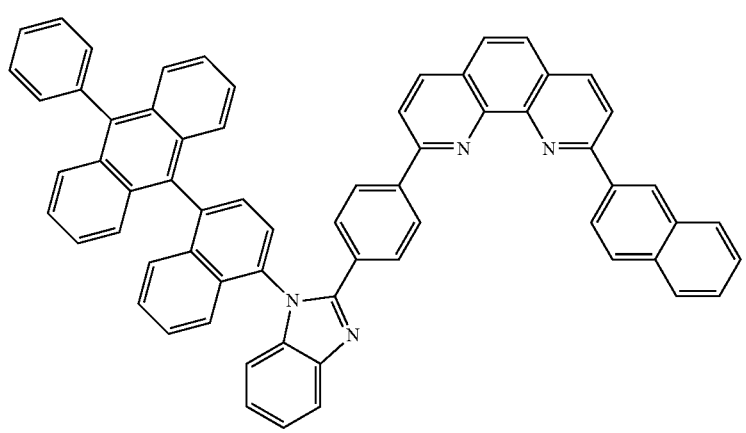

EX17

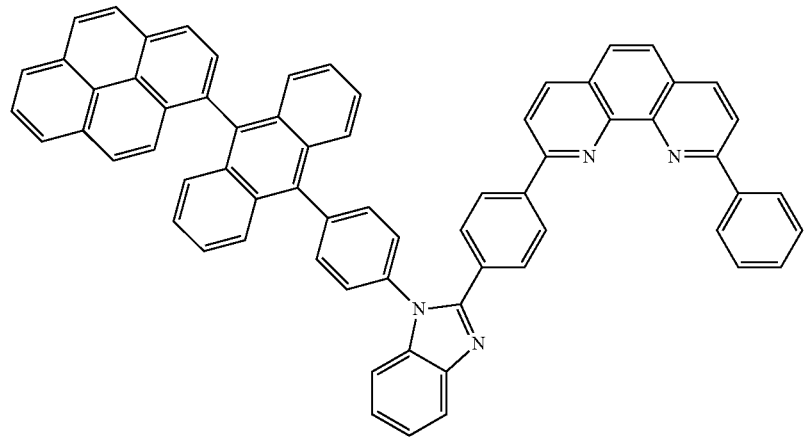

Detailed preparation for the phenanthroline derivative in the present invention could be clarified by exemplary embodiments, but the present invention is not limited to exemplary embodiments. EXAMPLE 1~3 show the preparation for examples of the phenanthroline derivative in the present invention. EXAMPLE 4 show the fabrication of organic EL device and I-V-B, half-life time of organic EL device testing report.

Example 1

Synthesis of EX1

Synthesis of 9-bromo-10-(naphthalen-1-yl)anthracene

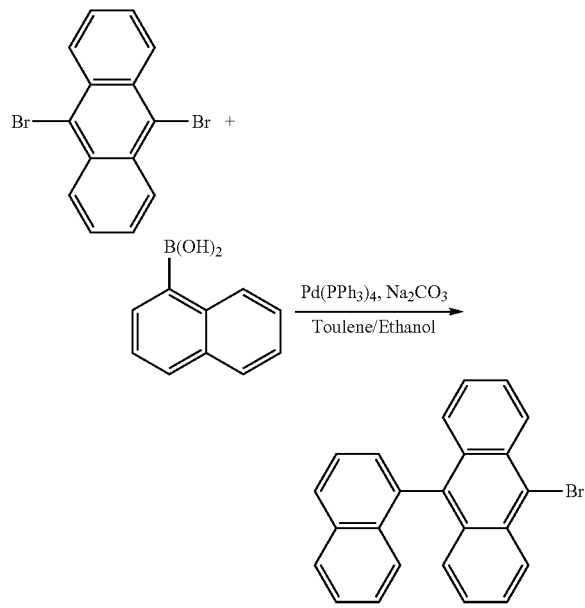

A mixture of 40 g (119 mmol) of 9,10-dibromoanthracene, 20.5 g (119 mmol) of naphthalen-1-ylboronic acid, 1.38 g (1.2 mmol) of Pd(PPh₃)₄, 120 ml of 2M Na₂CO₃, 200 ml of EtOH and 600 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (19.2 g, 50 mmol, 42%) as a yellow solid.

Synthesis of 4-(10-(naphthalen-1-yl)anthracen-9-yl)aniline

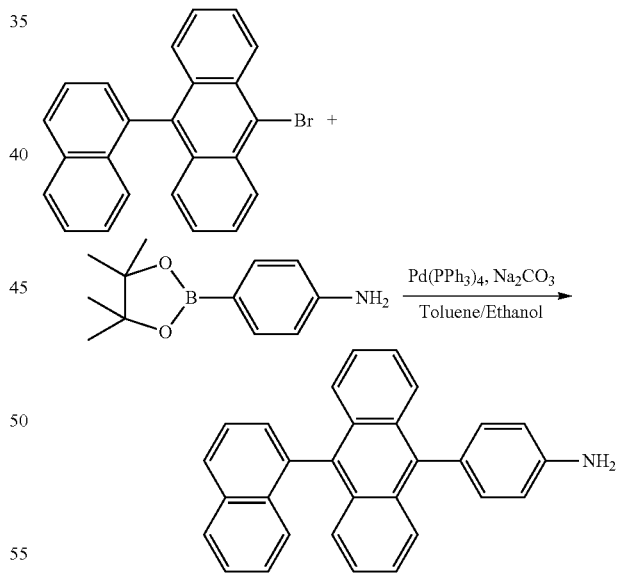

A mixture of 20 g (52.2 mmol) of 9-bromo-10-(naphthalen-1-yl)-anthracene, 13.7 g (62.6 mmol) of 4-(4,4,5,5-tetramethyl-1,3,2-dioxaborolan-2-yl)aniline, 0.6 g (0.52 mmol) of Pd(PPh₃)₄, 52 ml of 2M Na₂CO₃, 150 ml of EtOH and 450 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (12.8 g, 32.3 mmol, 62%) as a yellow solid.

Synthesis of N-(4-(10-(naphthalen-1-yl)anthracen-9-yl)phenyl)-2-nitroaniline

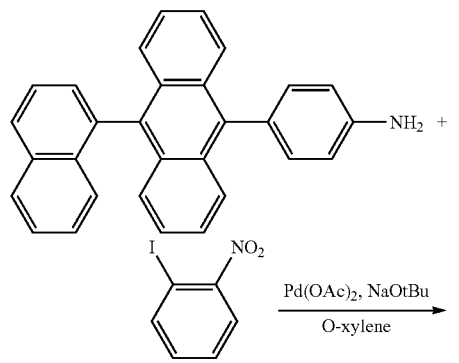

A mixture of 10 g (25.3 mmol) of 4-(10-(naphthalen-1-yl)anthracen-9-yl)aniline, 6.3 g (25.3 mmol) of 1-iodo-2-nitrobenzene, 56.7 mg (0.25 mmol) of Pd(OAc)$_2$, 4.86 g (50.6 mmol) of sodium tert-butoxide, 400 ml of O-xylene was degassed and placed under nitrogen, and then heated at 140° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (4.44 g, 8.6 mmol, 34%) as a brown solid.

Synthesis of N1-(4-(10-(naphthalen-1-yl)anthracen-9-yl)phenylbenzene-1,2-diamine

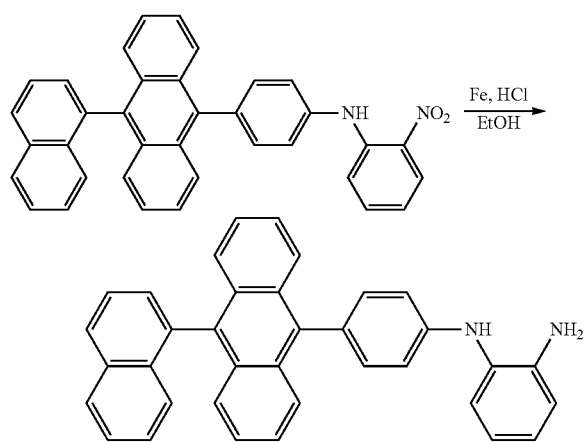

A mixture of 10 g (19.3 mmol) of N-(4-(10-(naphthalen-1-yl)anthracen-9-yl)phenyl)-2-nitroaniline, 3.24 g (58 mmol) of iron powder, 200 ml of ethanol was degassed and placed under nitrogen, and then heated at 80° C. for 30 min. 12.1 ml 37.5%(96.5 mmol) of hydrochloric acid was then added, and then heated at 80° C. for 12 h. After finishing the reaction, the mixture was allowed to cool to room temperature. 13 ml of ammonia solution, 21.8 g (77.2 mmole) of potassium sodium tartrate, and 600 ml water was added, and then stir for 30 min. The organic layer was extracted with dichloromethane and water, dried with anhydrous magnesium sulfate, the solvent was removed and the residue was purified by column chromatography on silica to give product (7.8 g, 16 mmol, 83%) as a brown solid.

Synthesis of 2-(4-bromophenyl)-1-(4-(10-(naphthalen-1-yl)anthraces-9-yl)phenyl)-1H-benzo[d]imidazole

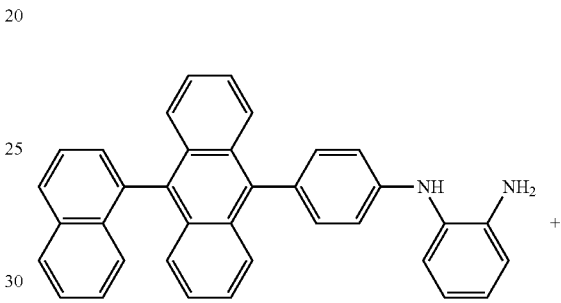

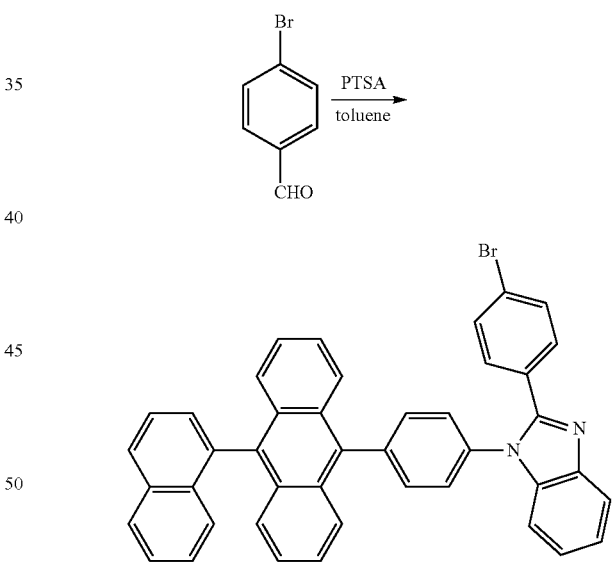

A mixture of 10 g (20.5 mmol) of N1-(4-(10-(naphthalen-1-yl)-anthracen-9-yl)phenyl)benzene-1,2-diamine, 4.56 g (24.7 mmol) of 4-bromo-benzaldehyde, 782 mg (4.1 mmol) of p-toluenesulfonic acid, 200 ml of anhydrous toluene was degassed and placed under nitrogen, and then heated at 110° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (3.74 g, 5.7 mmol, 28%) as a yellow solid.

Synthesis of 1-(4-(10-(naphthalen-1-yl)anthracen-9-yl)phenyl)-2-(4-(4,4,5,5-tetramethyl-1,3,2-dioxaborolan-2-yl)phenyl)-1H-benzo[d]imidazole

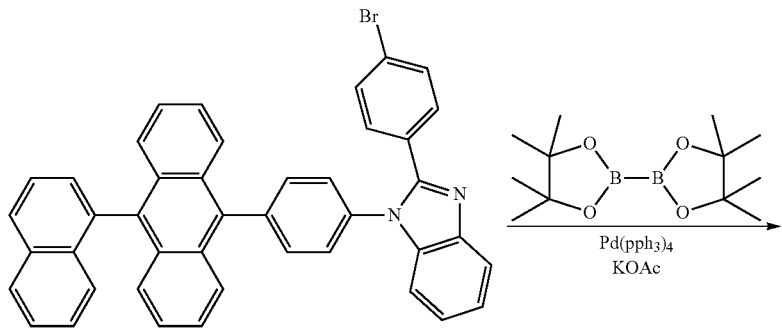

A mixture of 5 g (7.67 mmol) of 2-(4-bromophenyl)-1-(4(10-(naphthalen-1-yl)anthracen-9-yl)phenyl)-1H-benzo[d]imidazole, 2.14 g (8.4 mm ol) of 4,4,4',4',5,5,5',5'-octamethyl-2,2'-bi(1,3,2-dioxaborolane), 177 mg (0.15 mmol) of Pd(PPh$_3$)$_4$, 1.5 g(15.5 mmol) of potassium acetate, 100 ml of 1,4-dioxane was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (3.1 g, 4.4 mmol, 58%) as a yellow solid.

Synthesis of EX1

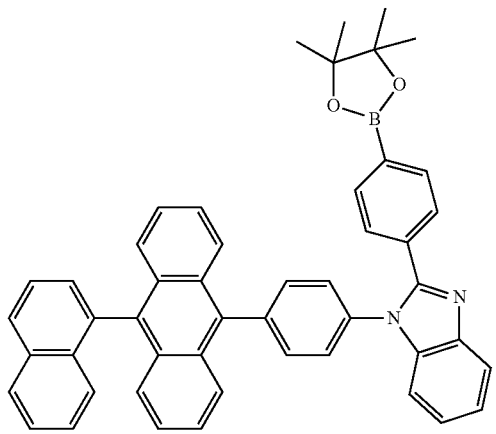

+

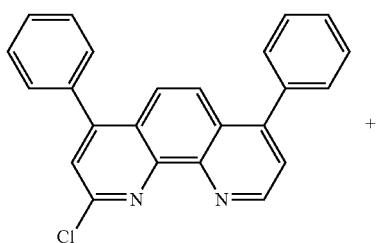

Pd(PPh$_3$)$_4$, Na$_2$CO$_3$

Toluene/Ethanol

-continued

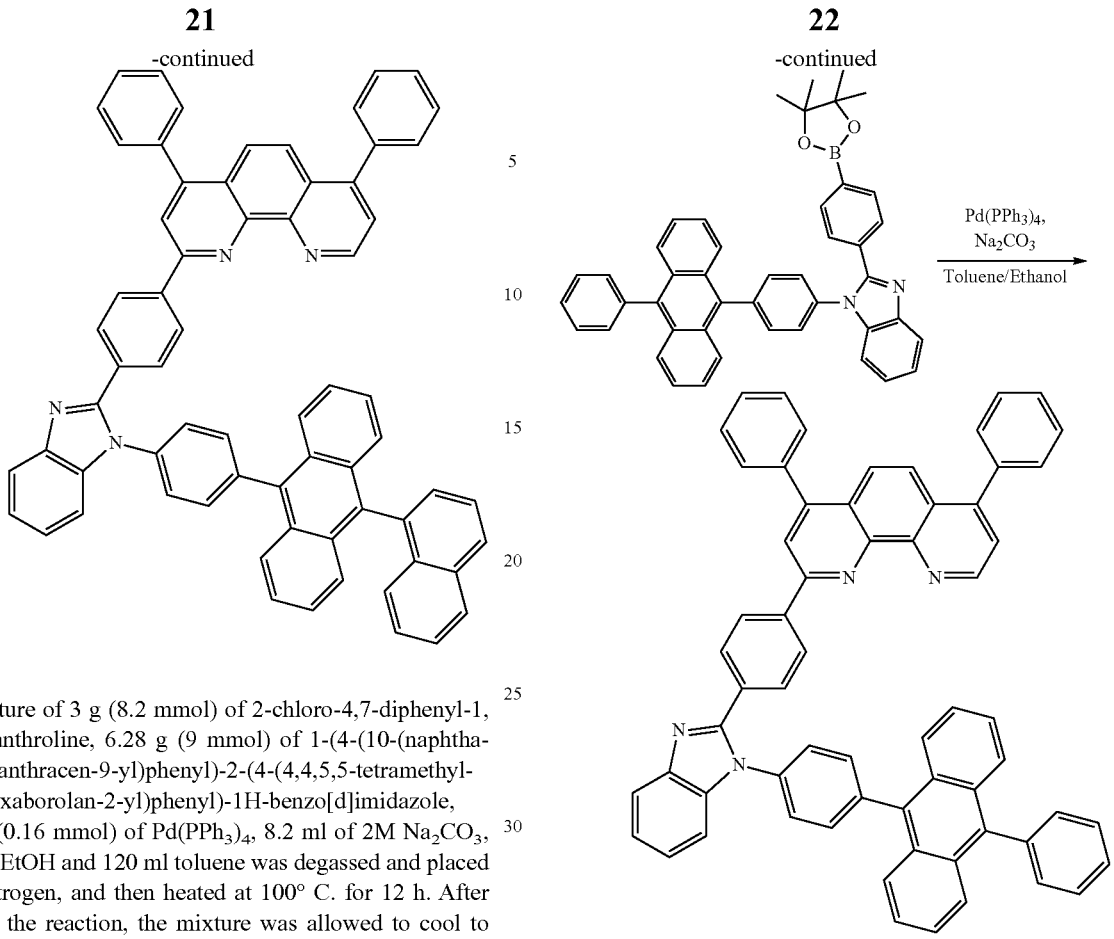

A mixture of 3 g (8.2 mmol) of 2-chloro-4,7-diphenyl-1,10-phenanthroline, 6.28 g (9 mmol) of 1-(4-(10-(naphthalen-1-yl)anthracen-9-yl)phenyl)-2-(4-(4,4,5,5-tetramethyl-1,3,2-dioxaborolan-2-yl)phenyl)-1H-benzo[d]imidazole, 189 mg (0.16 mmol) of Pd(PPh$_3$)$_4$, 8.2 ml of 2M Na$_2$CO$_3$, 40 ml of EtOH and 120 ml toluene was degassed and placed under nitrogen, and then heated at 100° C. for 12 h. After finishing the reaction, the mixture was allowed to cool to room temperature. The organic layer was extracted with dichloromethane and water, dried with anhydrous magnesium sulfate, the solvent was removed and the residue was purified by column chromatography on silica to give product (4.8 g, 5.3 mmol, 65%) as a yellow solid. MS (m/z, FAB$^+$): 902.8; $^1$H NMR (CDCl$_3$, 500 MHz): chemical shift (ppm) 8.69 (d, 2H), 8.49 (d, 2H), 8.23 (s, 1H), 8.17~8.11 (d, 2H), 7.89~7.83 (m, 4H), 7.80~7.68 (m, 6H), 7.65~7.49 (m, 14H), 7.45~7.41 (m, 2H), 7.40~7.27 (m, 9H).

Example 2

Synthesis of EX6

Synthesis of 4,7-diphenyl-2-(4-(1-(4-(10-phenylanthracen-9-yl)phenyl)-1H-benzo[d]imidazol-2-yl)phenyl)-1,10-phenanthroline

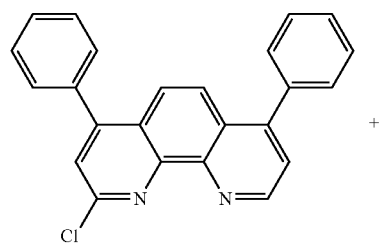 +

1-(4-(10-phenylanthracen-9-yl)phenyl)-2-(4-(4,4,5,5-tetramethyl-1,3,2-dioxaborolan-2-yl)phenyl)-1H-benzo[d]imidazole instead of 1-(4-(10-(naphthalen-1-yl)anthracen-9-yl)phenyl)-2-(4-(4,4,5,5-tetramethyl-1,3,2-dioxaborolan-2-yl)phenyl)-1H-benzo[d]imidazole, except for using the same method as in synthesis example 1, the desired compound of 4,7-diphenyl-2-(4-(1-(4-(10-phenylanthracen-9-yl)phenyl)-1H-benzo[d]imidazol-2-yl)phenyl)-1,10-phenanthroline (4.3 g, yield=62%) was obtained. MS (m/z, FAB$^+$): 852.8; $^1$H NMR (CDCl$_3$, 500 MHz): chemical shift (ppm) 8.68 (d, 2H), 8.50 (d, 2H), 8.25 (s, 1H), 8.19~8.13 (d, 2H), 7.91~7.82 (m, 4H), 7.78~7.68 (m, 6H), 7.65~7.48 (m, 12H), 7.46~7.42 (m, 2H), 7.40~7.28 (m, 9H).

Example 3

Synthesis of EX12

Synthesis of 2-(4-(1-(4-(10-(naphthalen-2-yl)anthracen-9-yl)phenyl)-1H-benzo[d]imidazol-2-yl)phenyl)-4,7-diphenyl-1,10-phenanthroline

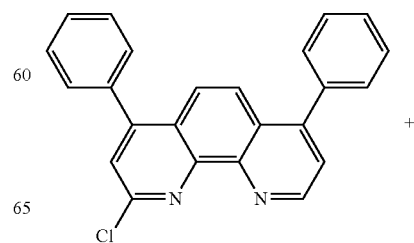 +

-continued

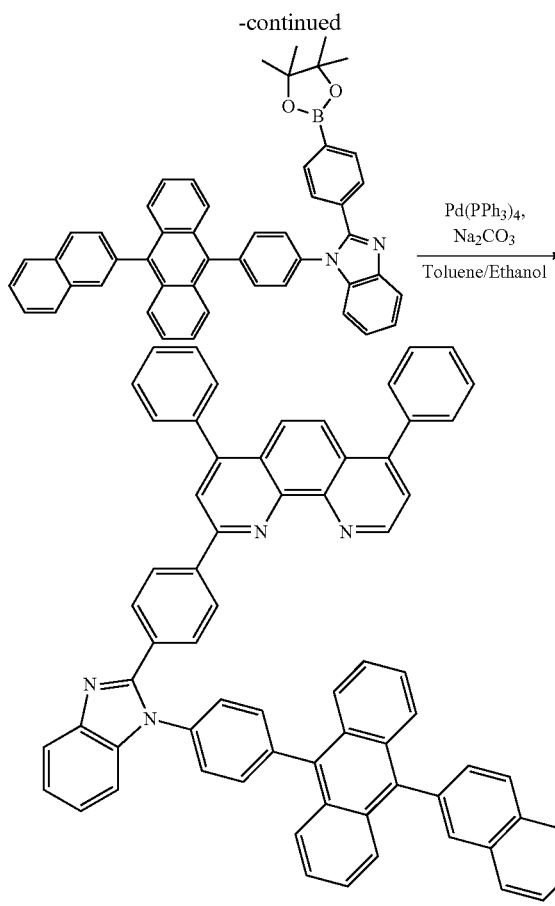

1-(4-(10-(naphthalen-2-yl)anthracen-9-yl)phenyl)-2-(4-(4,4,5,5-tetramethyl-1,3,2-dioxaborolan-2-yl)phenyl)-1H-benzo[d]imidazole instead of 1-(4-(10-(naphthalen-1-yl)anthracen-9-yl)phenyl)-2-(4-(4,4,5,5-tetramethyl-1,3,2-dioxaborolan-2-yl)phenyl)-1H-benzo[d]imidazole, except for using the same method as in synthesis example 1, the desired compound of -(4-(1-(4-(10-(naphthalen-2-yl)anthracen-9-yl)phenyl)-1H-benzo[d]imidazol-2-yl)phenyl)-4,7-diphenyl-1,10-phenanthroline (4.87 g, yield=66%) was obtained. MS (m/z, FAB+): 902.8; $^1$H NMR (CDCl$_3$, 500 MHz): chemical shift (ppm) 8.70 (d, 2H), 8.51 (d, 2H), 8.22 (s, 1H), 8.16~8.09 (d, 2H), 7.88~7.83 (m, 4H), 7.80~7.70 (m, 6H), 7.65~7.51 (m, 14H), 7.47~7.41 (m, 2H), 7.40~7.28 (m, 9H).

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, N,N-Bis(naphthalene-1-yl)-N,N-bis(phenyl)-benzidine (NPB) is most widely used as the hole transporting layer, 10,10-Dimethyl-12-(4-(pyren-1-yl)phenyl)-10H-indeno[1,2-b]triphenylene(PT-312, US20140175384) is used as blue emitting host in organic EL device and N1,N1,N6,N6-tetram-tolylpyrene-1,6-diamine (D1) is used as blue guest; 2-(10,10-dimethyl-10H-indeno[2,1-b]triphenylen-13-yl)-4,6-diphenyl-1,3,5-triazine(HB1), 2-(10,10-dimethyl-10H-indeno[2,1-b]triphenylen-12-yl)-4,6-diphenyl-1,3,5-triazine(HB2) and HB3 (see the following chemical structure) are used as hole blocking material (HBM); 4,7-diphenyl-2-(411-phenyl-1H-benzo[d]imidazol-2-yl)phenyl)-1,10-phenanthroline (ET1) and 2,9-di(naphthalen-2-yl)-4,7-diphenyl-1,10-phenanthroline (ET2) are used as electron transporting material (ET1) to co-deposit with 5% Li, or co-deposit with 8-hydroxyquinolato-lithium (LiQ) in organic EL device for comparison. The prior art of OLED materials for producing standard organic EL device control and comparable material in this invention shown its chemical structure as follows:

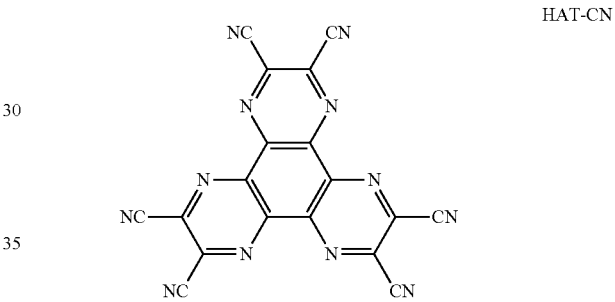

HAT-CN

NPB

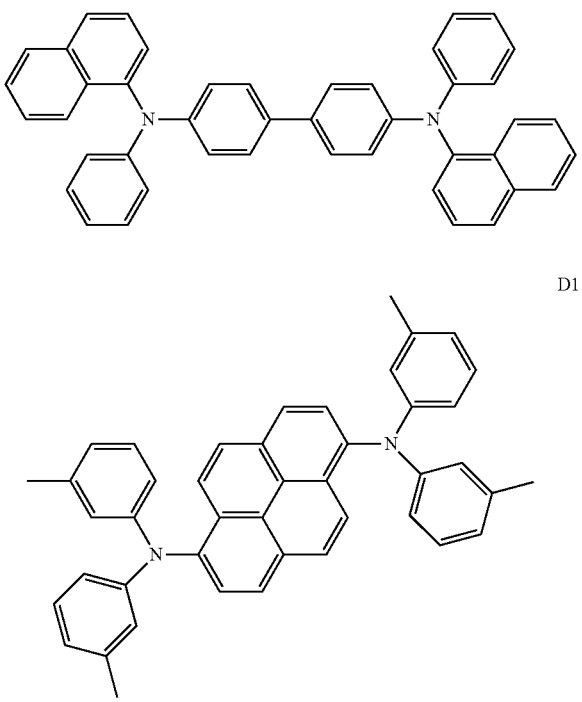

D1

PT-312
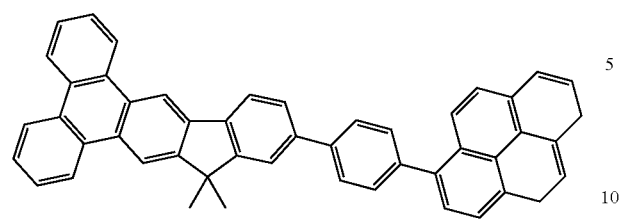
LiQ
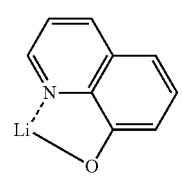
HB1
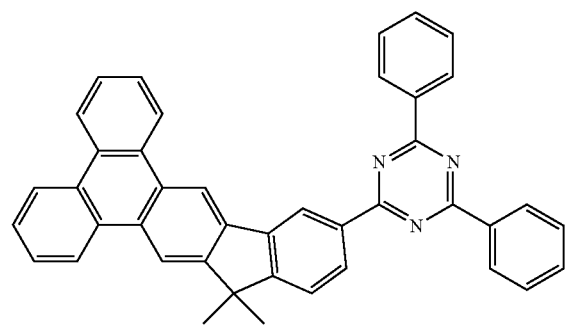
HB2
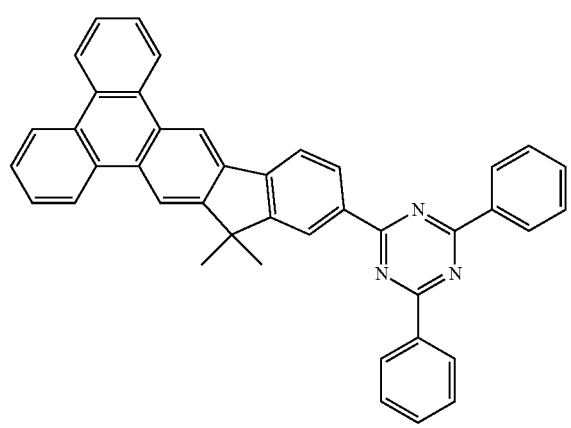
HB3
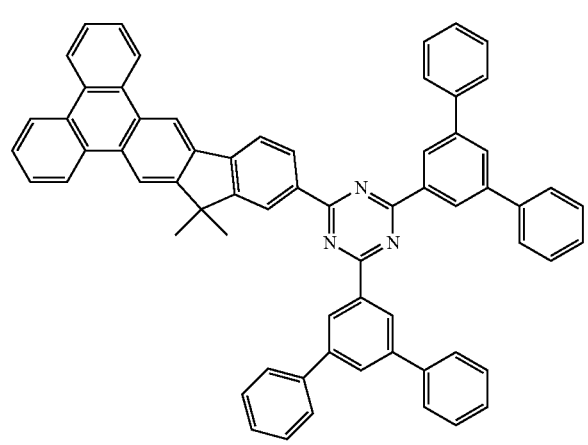
ET1
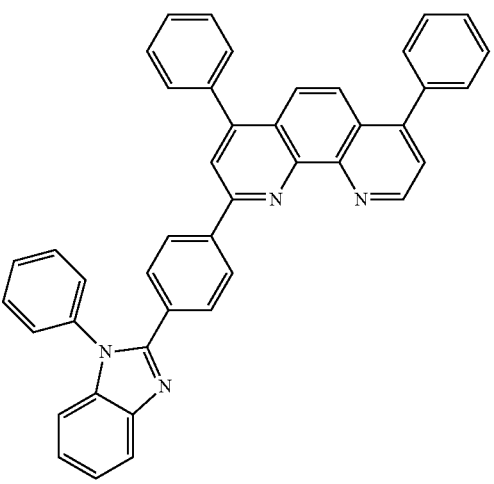
ET2
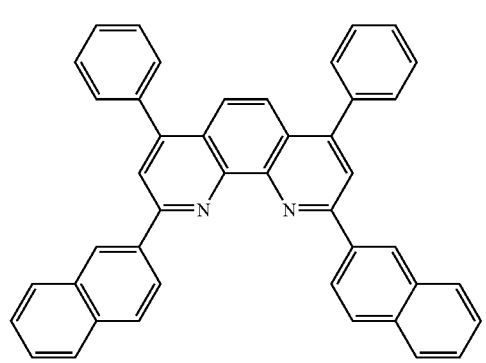
EX1
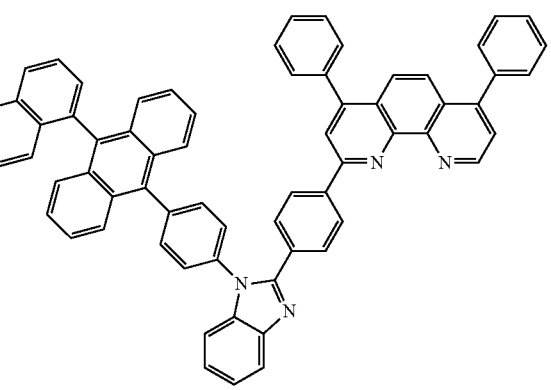
EX6
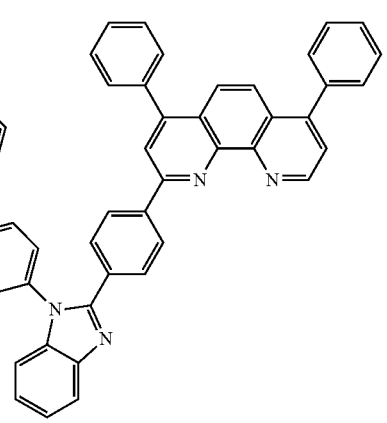

EX12

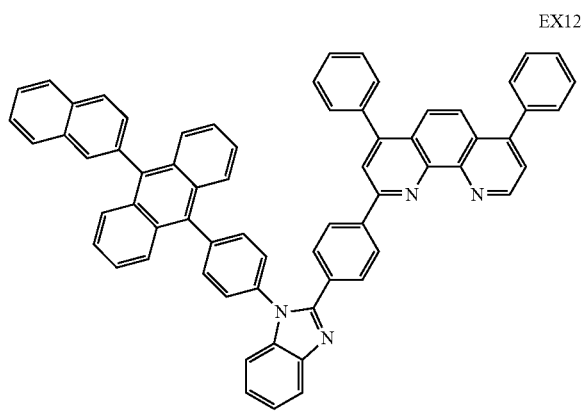

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 4

Using a procedure analogous to the above mentioned general method, fluorescent blue-emitting organic EL device having the following device structure I and II was produced (See FIG. 1). Device I: ITO/HAT-CN (20 nm)/NPB(110 nm)/PT-312 doped 5% D1(30 nm)/HBM/ETM doped 5% Li(35 nm)/Al(160 nm). Device II: ITO/HAT-CN(20 nm)/NPB(110 nm)/PT-312 doped 5% D1(30 nm)/HBM/ETM co-deposit 50% LiQ(40 nm)/LiQ (1 nm)/Al (160 nm). The I-V-B (at 1000 nits) and half-life time of fluorescent blue-emitting organic EL device testing report as Table1 and Table2. The half-life time is defined that the initial luminance of 1000 cd/m² has dropped to half.

TABLE 1

| HBM | ETM doped 5% Li | Voltage (V) | Efficiency (cd/A) | CIE (y) | Half-life time (hour) |
|---|---|---|---|---|---|
| HB1 | ET1 | 6.2 | 3.8 | 0.176 | 150 |
| HB1 | ET2 | 6.5 | 3.9 | 0.178 | 160 |
| HB1 | EX1 | 4.8 | 5.5 | 0.172 | 350 |
| HB1 | EX6 | 4.5 | 4.9 | 0.173 | 280 |
| HB1 | EX12 | 4.5 | 6.3 | 0.173 | 350 |
| — | EX12 | 4.6 | 6.0 | 0.172 | 300 |
| HB2 | EX1 | 4.0 | 6.5 | 0.173 | 450 |

TABLE 2

| HBM | ETM co-deposit 50% LiQ | Voltage (V) | Efficiency (cd/A) | CIE (y) | Half-life time (hour) |
|---|---|---|---|---|---|
| HB3 | ET1 | 7.0 | 4.6 | 0.189 | 180 |
| HB3 | ET2 | 6.6 | 4.3 | 0.188 | 160 |
| HB3 | EX1 | 5.8 | 6.2 | 0.181 | 480 |
| HB3 | EX6 | 4.9 | 5.1 | 0.180 | 360 |
| HB3 | EX12 | 4.3 | 6.6 | 0.181 | 450 |
| — | EX12 | 4.6 | 6.1 | 0.182 | 400 |
| HB2 | EX1 | 4.5 | 6.9 | 0.180 | 510 |

In the above preferred embodiments for organic EL device test report (see Table 1 to Table 2), we show that the phenanthroline derivative with a general formula(I) used as hole blocking electron transport material or electron transport material for organic EL in the present invention display good performance than the prior art of organic EL materials. More specifically, the organic EL device in the present invention use the phenanthroline derivative with a general formula(I) as electron transport material to collocate with hole blocking material such as HB1, HB2 and HB3 shown lower power consumption, higher efficiency and longer half-life time. Besides the organic EL device in the present invention use the phenanthroline derivative with a general formula(I) also can use as hole blocking electron transport material without collocate with hole blocking material and shown good performance than prior art of organic EL materials To sum up, the present invention discloses a phenanthroline derivative with a general formula(I) used as hole blocking electron transport material or electron transport material for organic EL device. The mentioned phenanthroline derivative are represented by the following formula(I)

formula(I)

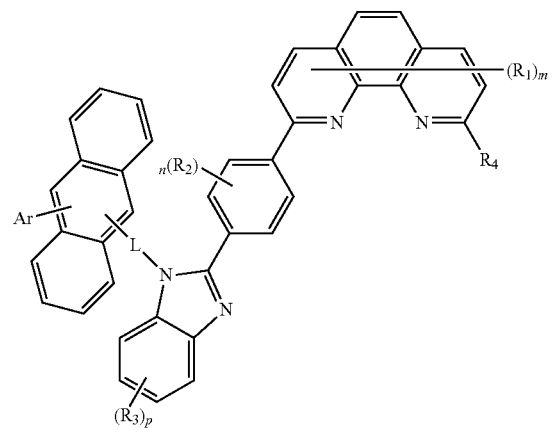

wherein L represents a substituted or unsubstituted arylene group having 6 to 30 ring carbon atoms, m represents an integer of 0 to 6, n represents an integer of 0 to 4, p represents an integer of 0 to 4; Ar is a substituted or unsubstituted aryl group having 6 to 50 ring carbon atoms, provided that Ar represents a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, and a substituted or unsubstituted chrysenyl group; $R_1$ to $R_4$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A phenanthroline derivative represented by the following formula(I):

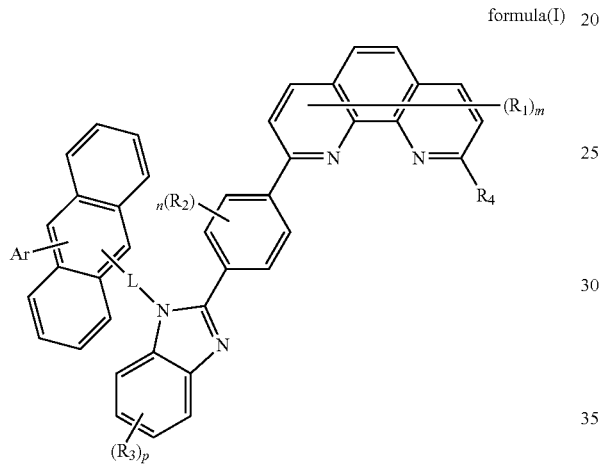

formula(I)

wherein L represents a substituted or unsubstituted arylene group having 6 to 30 ring carbon atoms, m represents an integer of 0 to 6, n represents an integer of 0 to 4, p represents an integer of 0 to 4; Ar is a substituted or unsubstituted aryl group having 6 to 50 ring carbon atoms, provided that Ar represents a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, and a substituted or unsubstituted chrysenyl group; $R_1$ to $R_4$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

2. The phenanthroline derivative according to claim 1, wherein Ar is represented by the following formulas:

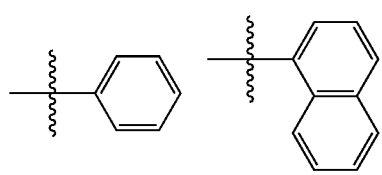

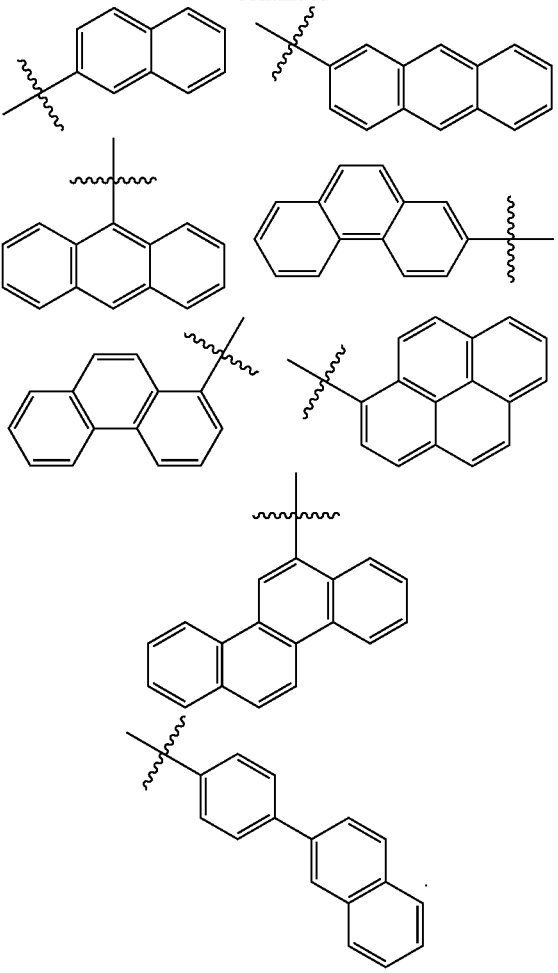

3. The phenanthroline derivative according to claim 1, wherein the phenanthroline derivative formula(I) is represented by the following formula(II):

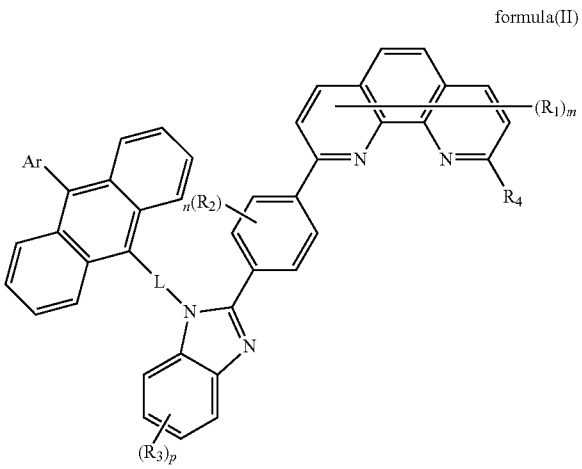

formula(II)

wherein L represents a substituted or unsubstituted arylene group having 6 to 30 ring carbon atoms, m represents an integer of 0 to 6, n represents an integer of 0 to 4, p represents an integer of 0 to 4; Ar is a substituted or unsubstituted aryl group having 6 to 50 ring carbon atoms, provided that Ar represents a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, and a substituted or unsubstituted chrysenyl group; $R_1$ to $R_4$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

4. The phenanthroline derivative according to claim 3, wherein Ar is represented by the following formulas:

5. A organic electroluminescent device comprising a pair of electrodes consisting of a cathode and an anode and between the pairs of electrodes comprising at least a layer of the phenanthroline derivative with a general formula(I) according to claim 1.

6. The organic electroluminescent device according to claim 5, wherein the electron transport layer comprising the phenanthroline derivative with a general formula(I).

7. The organic electroluminescent device according to claim 5, wherein the hole blocking electron transport layer comprising the phenanthroline derivative with a general formula(I).

8. The organic electroluminescent device according to claim 5, wherein the hole blocking layer comprising the following formulas:

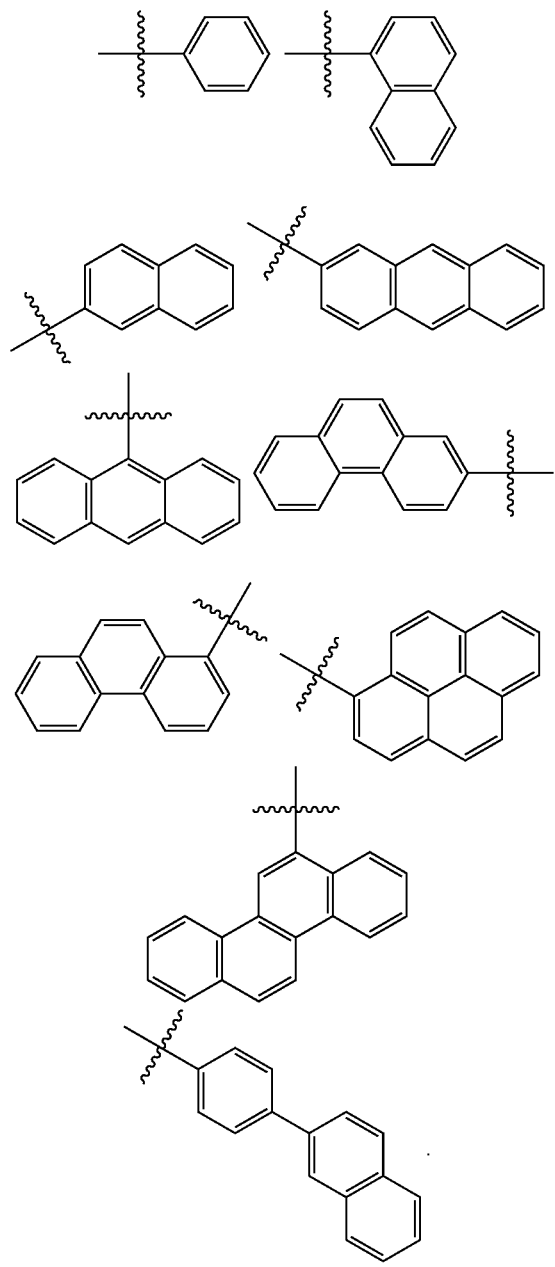

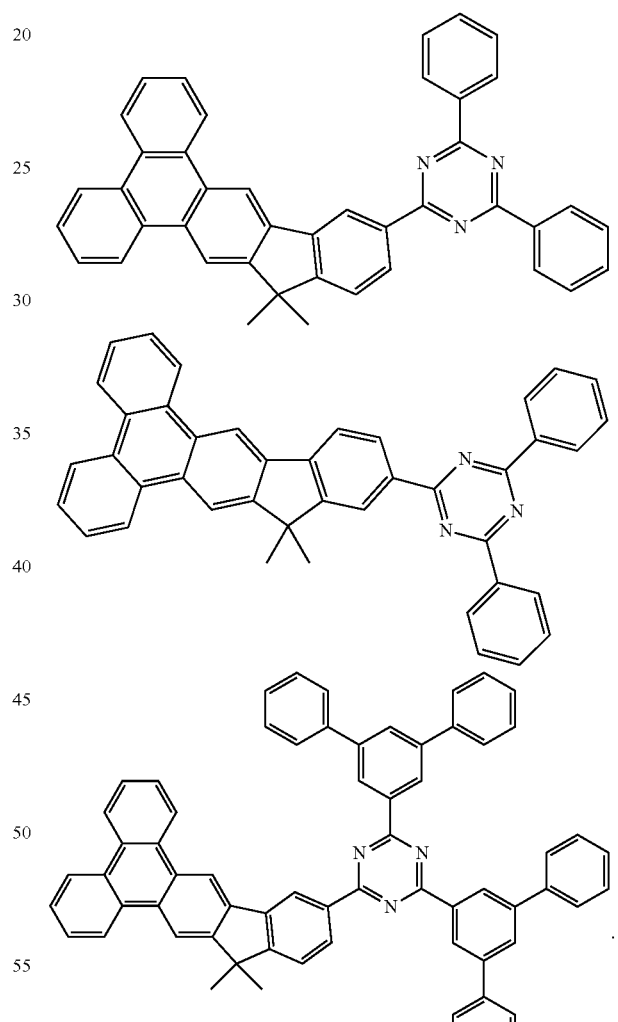

9. The organic electroluminescent device according to claim 6, wherein the electron transport layer comprising lithium or 8-hydroxyuinolinolato-lithium.

10. The phenanthroline derivative according to claim 1, wherein the phenanthroline derivative is selected from the formula consisting of:

EX1 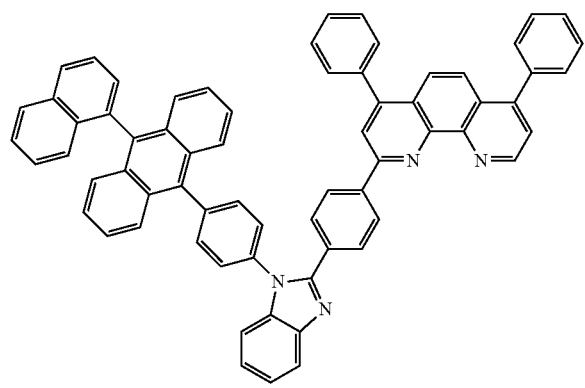
EX2 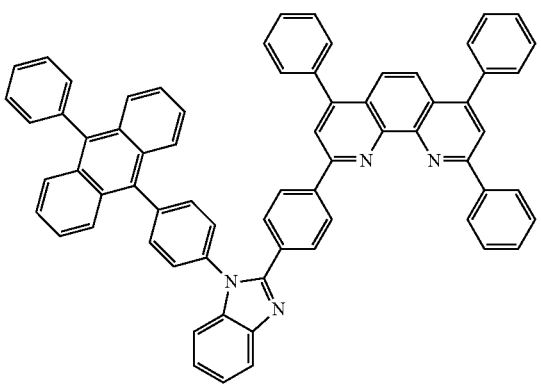
EX3 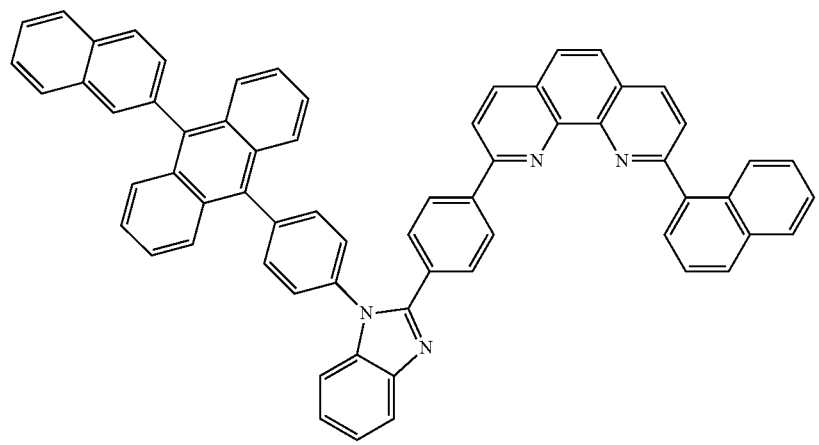
EX4 EX5 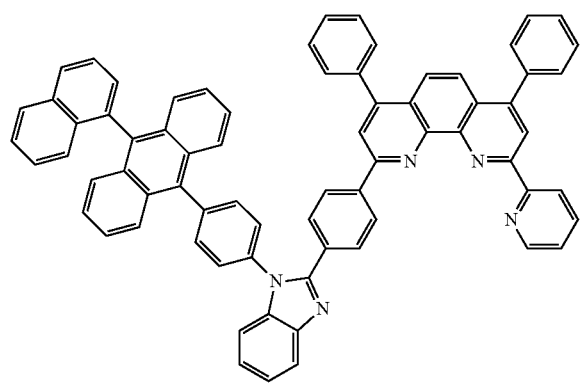

-continued
EX6
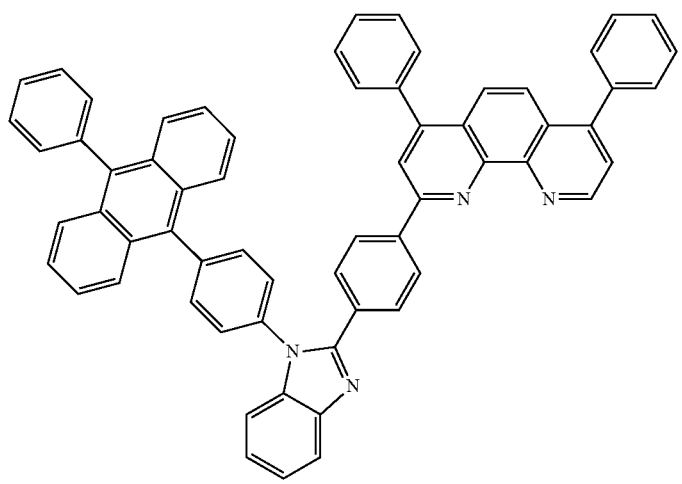
EX7
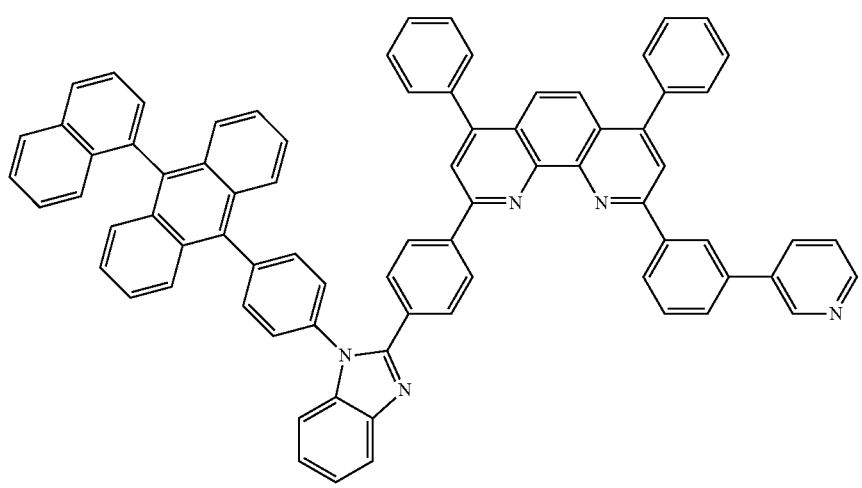
EX8
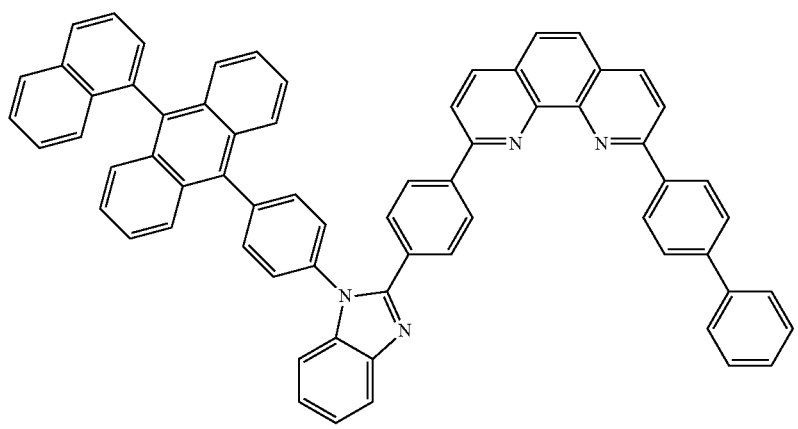

-continued
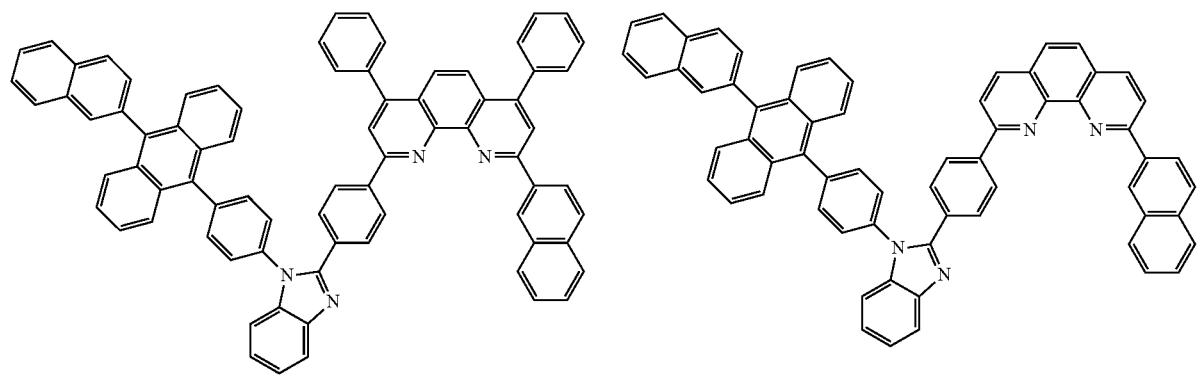
EX9　　　EX10
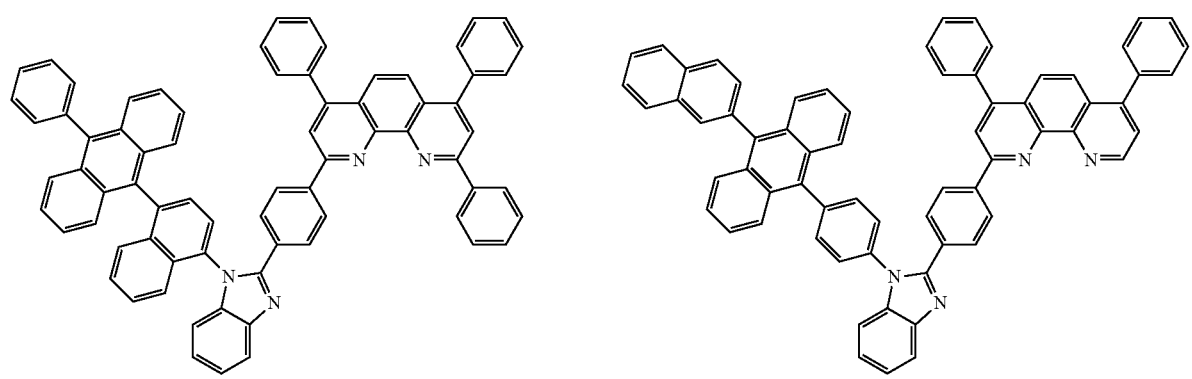
EX11　　　EX12
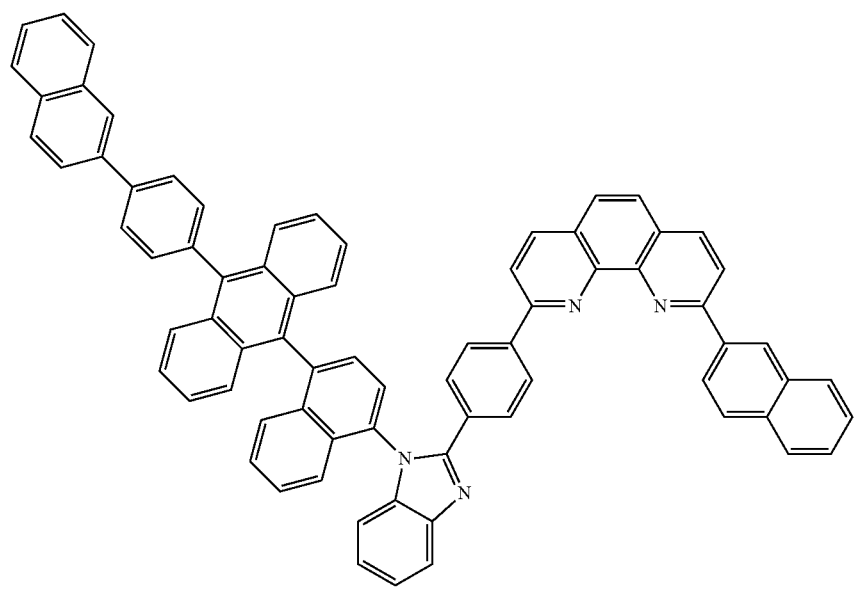
EX13

EX14
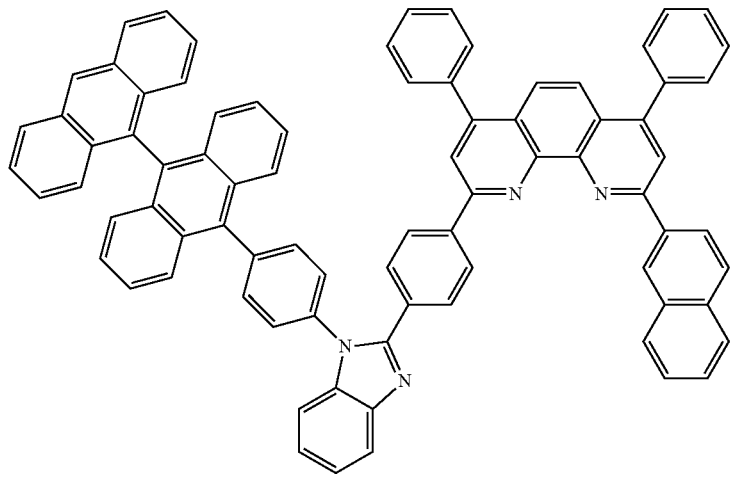
EX15
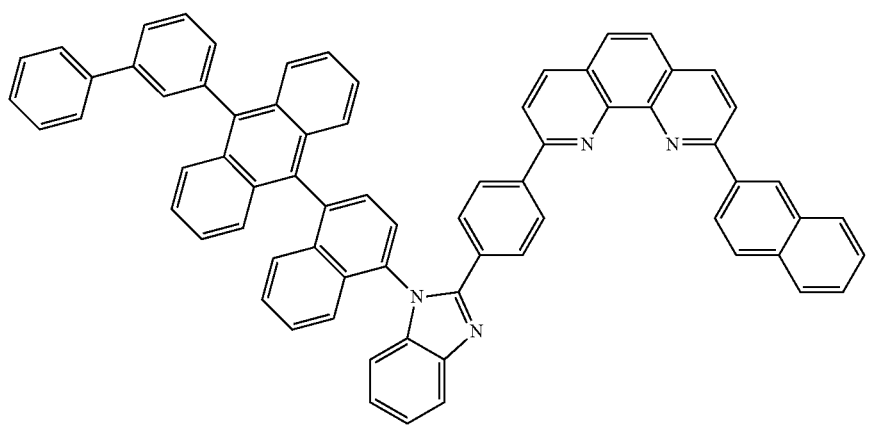
EX16
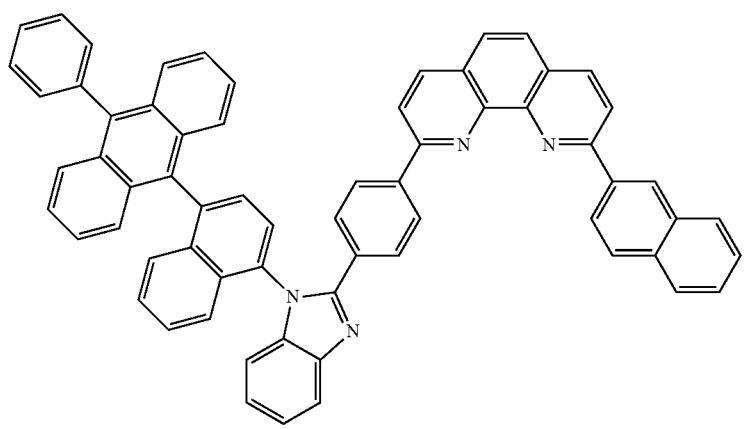
and

-continued
EX17
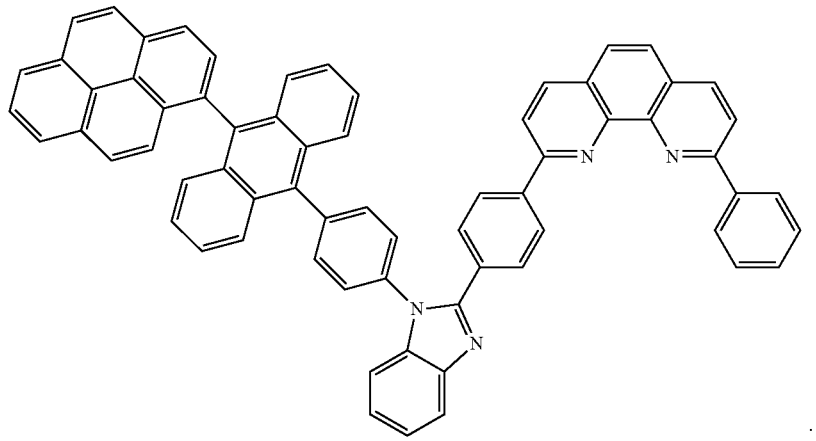
* * * * *